(12) United States Patent
Park et al.

(10) Patent No.: US 8,962,703 B2
(45) Date of Patent: Feb. 24, 2015

(54) PREPARATION OF IRON/CARBON NANOCOMPOSITE CATALYSTS FOR FISCHER-TROPSCH SYNTHESIS REACTION AND RELATED PRODUCTION OF LIQUID HYDROCARBONS

(71) Applicant: Korea Institute of Energy Research, Daejeon (KR)

(72) Inventors: Jichan Park, Daejeon (KR); Heon Jung, Daejeon (KR); Hotae Lee, Daejeon (KR); Jungil Yang, Daejeon (KR); Donghyun Chun, Daejeon (KR); Sungjun Hong, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 109 days.

(21) Appl. No.: 13/925,361

(22) Filed: Jun. 24, 2013

(65) Prior Publication Data
US 2013/0341242 A1      Dec. 26, 2013

(30) Foreign Application Priority Data

Jun. 25, 2012   (KR) .................. 10-2012-0068034

(51) Int. Cl.
C07C 1/04        (2006.01)
C10G 2/00        (2006.01)
B01J 27/22       (2006.01)
B01J 23/745      (2006.01)

(52) U.S. Cl.
CPC ............ *C07C 1/044* (2013.01); *C10G 2/332* (2013.01); *C07C 1/0445* (2013.01); *C07C 2527/22* (2013.01); *B01J 27/22* (2013.01)
USPC ........... 518/719; 502/177; 502/185; 518/720

(58) Field of Classification Search
CPC  C07C 2527/22; C07C 1/0444; C07C 1/0445; C10G 2/332; B01J 27/22; B01J 37/0201; B01J 37/0081
USPC .................................. 502/177, 185; 518/720
See application file for complete search history.

(56) References Cited

U.S. PATENT DOCUMENTS

2010/0300984 A1\*  12/2010  Kastner et al. ............... 210/763
2012/0115715 A1\*   5/2012  Wolters et al. ............... 502/240

\* cited by examiner

*Primary Examiner* — Melvin C Mayes
*Assistant Examiner* — James Corno
(74) *Attorney, Agent, or Firm* — Lowe Hauptman & Ham, LLP

(57) ABSTRACT

Iron/carbon (Fe/C) nanocomposite catalysts are prepared for Fischer-Tropsch synthesis reaction. A preparation method includes steps of mixing iron hydrate salts and a mesoporous carbon support to form a mixture, infiltrating the iron hydrate salts into the carbon support through melt infiltration of the mixture near a melting point of the iron hydrate salts, forming iron-carbide particles infiltrated into the carbon support through calcination of the iron hydrate salts infiltrated into the carbon support under a first atmosphere, and vacuum-drying the iron-carbide particles after passivation using ethanol. Using such catalysts, liquid hydrocarbons are produced.

14 Claims, 12 Drawing Sheets

PREPARATION OF IRON/CARBON NANOCOMPOSITE CATALYSTS FOR FISCHER-TROPSCH SYNTHESIS REACTION AND RELATED PRODUCTION OF LIQUID HYDROCARBONS

CROSS REFERENCE TO RELATED APPLICATION

This application claims the priority of Korean Patent Application No. 10-2012-0068034, filed on Jun. 25, 2012in the Korean Intellectual Property Office (KIPO), the disclosure of which is incorporated herein in their entirety by reference.

BACKGROUND OF THE INVENTION

1. Field of the Invention

The present invention relates generally to high temperature Fischer-Tropsch technology and, more particularly, to a preparation of iron/carbon (Fe/C) nanocomposite catalysts for Fischer-Tropsch synthesis reaction and a related production of liquid hydrocarbons.

2. Description of the Related Art

Fischer-Tropsch (hereinafter abbreviated to FT) synthesis technology was first developed by two German chemists Franz Fischer and Hans Tropsch in the 1920s. The FT process produces synthetic fuels (i.e., hydrocarbon) from synthetic gas (i.e., hydrogen and carbon monoxide) through the following reaction: $(2n+1)H_2+nCO \rightarrow C_nH_{(2n+2)}+nH_2O$. In the FT synthesis reaction that usually uses cobalt- or iron-based catalysts, reaction conditions such as a reaction temperature, a reaction pressure and gas composition depend on the type of catalyst used. Such FT synthesis reactions are often divided, according to their operation temperature, into low temperature FT (LTFT) operating at 200~250° C. and high temperature FT (HTFT) at 300~350° C. (Andrei Y. Khodakov et al, Chem. Rev., 2007, 107, 1672). Typically, in case of LTFT, cobalt-based catalysts with a relatively longer lifespan are used.

Cobalt-based catalysts have disadvantages such as the risk of poisoning caused by sulfur compounds and relatively high cost, while having advantages such as high activity and long lifespan. Further, cobalt-based catalysts have little activity to the water-gas shift (WGS) reaction, so that the ingredient ratio of synthetic gas (hydrogen and carbon monoxide in the proportion 2:1) exerts a strong influence on the FT reactions. On the contrary, iron-based catalysts having activity to the water-gas shift reaction can be used as various compositions in which the ingredient ratio of hydrogen and carbon monoxide varies between 1 and 2, and further used even under the existence of carbon dioxide. Therefore, in case of the high temperature FT reaction which is commercially applied on a large scale, iron-based catalysts have been usually used due to their advantages such as low cost and less weak sulfur tolerance.

Iron-based catalysts used for the low temperature FT reaction have been often prepared using a co-precipitation method (Korean Patent No. 10-1087165 titled "The method for preparing of Fe based catalyst used in Fischer-Tropsch synthesis reaction and that of liquid hydrocarbon using Fe based catalyst"). This catalyst has merits such as high iron content by weight with regard to total catalyst, but has several demerits such as complicated preparation process, low reliability, catalyst coking due to carbon monoxide, and poor stability at a high temperature. On the contrary, the high temperature FT reaction applied to produce light naphtha or gasoline has usually used fused Fe particles in a commercial process, and also has often used supported catalysts using supports in a laboratory-scale research stage (Qinghong Zhang et. al., ChemCatChem 2010, 2, 1030). Fused Fe applied to a commercial process has high mechanical strength because it is prepared through a melting process at a very high temperature more than 1000° C. However, it has been known as having some demerits such as a small crystal size and low activity (Hiroshige Matsujioto et. al., J. Catal. 1978, 53, 331).

Supported catalysts have been initially prepared through a wetness-impregnation method as disclosed in Korean Patent Publication No. 10-2011-0109625 titled "A noble catalyst of aqueous phase reforming reaction using mesoporous alumina carrier and platinum and manufacturing method thereof" and Korean Patent Publication No. 10-2011-0109624 titled "A noble catalyst of aqueous phase reforming reaction using mesoporous carbon carrier and multi-component metal and manufacturing method thereof". However, such wet type methods not only should select a suitable solvent for each metal salt to obtain catalysts with uniformly dispersed active particles, but also repeatedly require absorption and dry steps. Unfortunately, this process using a solvent may often invite the danger of work, environmental pollution, and a burden of solvent treatment at the mass production of catalysts.

Additionally, in case of conventional catalysts, it is required to activate catalyst particles of inactive iron oxide through a reduction process in a reactor. Therefore, a longer activation time of about 24 hours is unfavorably needed, and also such reduction or activation conditions negatively affect the activity of catalyst (Dragomir B. Bukur, J. Catal. 1995, 155, 353).

BRIEF SUMMARY OF THE INVENTION

Accordingly, the present invention is to address the above-mentioned problems and/or disadvantages and to offer at least the advantages described below.

One aspect of the present invention is to provide a method for uniformly dispersing iron hydrate salt into a support through a melt-infiltration process by using a great pore volume of a carbon support. Especially, activated charcoal, one of mesoporous carbon materials used for this invention, has a very large surface area of 1010 $m^2/g$ and a great pore volume of 0.85 $cm^3/g$, so that it has suitable characteristics for a carbon mold employed as a catalyst support.

Another aspect of the present invention is to provide iron/carbon nanocomposite catalysts activated by means of ex-situ activation. By obtaining activated catalysts through an ex-situ activation process under a carbon monoxide atmosphere in a state where iron hydrate salt is dispersed in a support, it is possible to reduce a time required for activation performed in a reactor. Furthermore, ex-situ catalyst activation can enhance the reliability of catalysts by minimizing variations according to reduction conditions.

Still another aspect of the present invention is to provide highly active, thermally stable iron/carbon nanocomposite catalysts suitable for high temperature FT reactions performed at 300° C. or more, to provide a preparation method of catalysts for selectively producing gasoline at a high temperature, and to provide reaction conditions suitable for such catalysts.

Yet another aspect of the present invention is to provide a production method of liquid hydrocarbons, based on a high CO conversion rate and selectivity by using iron/carbon nanocomposite catalysts.

According to one aspect of the present invention, provided is a method for preparing iron/carbon nanocomposite catalysts for Fischer-Tropsch synthesis reactions. This method includes steps of mixing iron hydrate salts and a mesoporous carbon support to form a mixture; infiltrating the iron hydrate salts into the carbon support through melt infiltration of the mixture near a melting point of the iron hydrate salts; forming iron-carbide particles infiltrated into the carbon support through calcination of the iron hydrate salts infiltrated into the carbon support under a first atmosphere; and vacuum-drying the iron-carbide particles after passivation using ethanol.

The method may further include steps of, between the infiltrating step and the particle forming step, drying the melt-infiltrated mixture; and removing parts of the carbon support and forming iron oxide by calcining the dried mixture in a second atmosphere.

In the method, the melting point of the iron hydrate salts may range between 30~100° C., and the iron hydrate salt may be one of $Fe(NO_3)_3 9H_2O$, $FeCl_3 6H_2O$ and $FeSO_4 7H_2O$.

In the method, the support may be mesoporous carbon having a pore volume of 0.2 cm³/g or more, and the iron hydrate salts may be added at the ratio of 0.5~4.5 with regard to the weight of the carbon support.

In the method, an ex-situ activation temperature of the catalysts may range between 300~600° C., and an ex-situ activation time of the catalysts may range between 1~24 hours.

In the method, the second atmosphere may be one of an air atmosphere, an oxygen atmosphere, and a mixed oxygen atmosphere of inert gas and oxygen.

In the method, the mixing step may include grinding the iron hydrate salts and the carbon support.

In the method, the infiltrating step may be performed at an operating temperature greater by 2~5° C. than the melting point of the salt in a closed system.

According to another aspect of the present invention, provided are iron/carbon nanocomposite catalysts prepared by the above-discussed method.

According to still another aspect of the present invention, provided is a method for producing liquid hydrocarbons using Fischer-Tropsch synthesis reactions. This method includes steps of loading the iron/carbon nanocomposite catalysts prepared by the method of claim 1 into a fixed-bed reactor; and injecting synthetic gas into the fixed-bed reactor at a high temperature without additional reduction or activation process.

In this method, the synthetic gas may be injected into the fixed-bed reactor at a gas hourly space velocity (GHSV) ranging between 3.0~15.0 $NL/g_{cat}/hr$.

According to yet another aspect of the present invention, provided are liquid hydrocarbons produced by the above-discussed method.

In various aspects of this invention, high-active iron/carbon nanocomposite catalysts for high temperature FT reactions can be prepared through a melt-infiltration method and an ex-situ activation process under a carbon monoxide atmosphere and thus can be obtained easily, quickly and in large amounts in comparison with a conventional co-precipitation method.

Further, in aspects of this invention, no use of additional solvent can improve work stability and reduce a burden of environmental pollution due to solvent treatment.

Also, in aspects of this invention, thermally stable, optimum, high-active, iron/carbon-supported catalysts can be obtained through easy controls of particle size, supported content, particle crystallizability, etc.

And also, in aspects of this invention, liquid hydrocarbons which are structurally stable to heat during high temperature FT reactions of 300° C. or more can be obtained selectively in a gasoline range and high yield on the basis of the above catalysts. Besides, no formation of solid-phase wax allows liquid hydrocarbons to be applied immediately without a hydrocracking process.

Other aspects, advantages, and salient features of the invention will become apparent to those skilled in the art from the following detailed description, which, taken in conjunction with the annexed drawings, discloses exemplary embodiments of the invention.

DETAILED DESCRIPTION OF THE INVENTION

Exemplary, non-limiting embodiments of the present invention will now be described more fully with reference to the accompanying drawings. This invention may, however, be embodied in many different forms and should not be construed as limited to the exemplary embodiments set forth herein. Rather, the disclosed embodiments are provided so that this disclosure will be thorough and complete, and will fully convey the scope of the invention to those skilled in the art. The principles and features of this invention may be employed in varied and numerous embodiments without departing from the scope of the invention.

Furthermore, well known or widely used techniques, elements, structures, and processes may not be described or illustrated in detail to avoid obscuring the essence of the present invention. Although the drawings represent exemplary embodiments of the invention, the drawings are not necessarily to scale and certain features may be exaggerated or omitted in order to better illustrate and explain the present invention.

Figure 1:
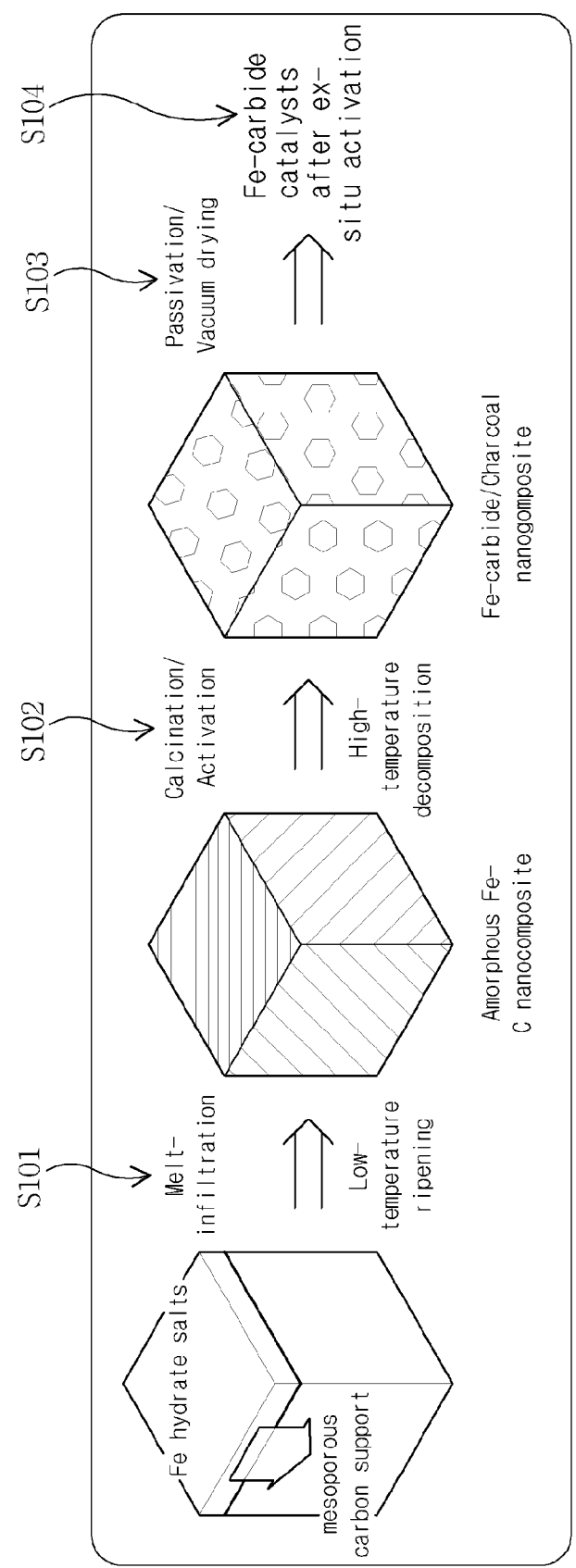
FIG. 1 is a schematic view illustrating a preparation of iron/carbon nanocomposite catalysts for Fischer-Tropsch reactions in accordance with an embodiment of the present invention.
Figure 2:
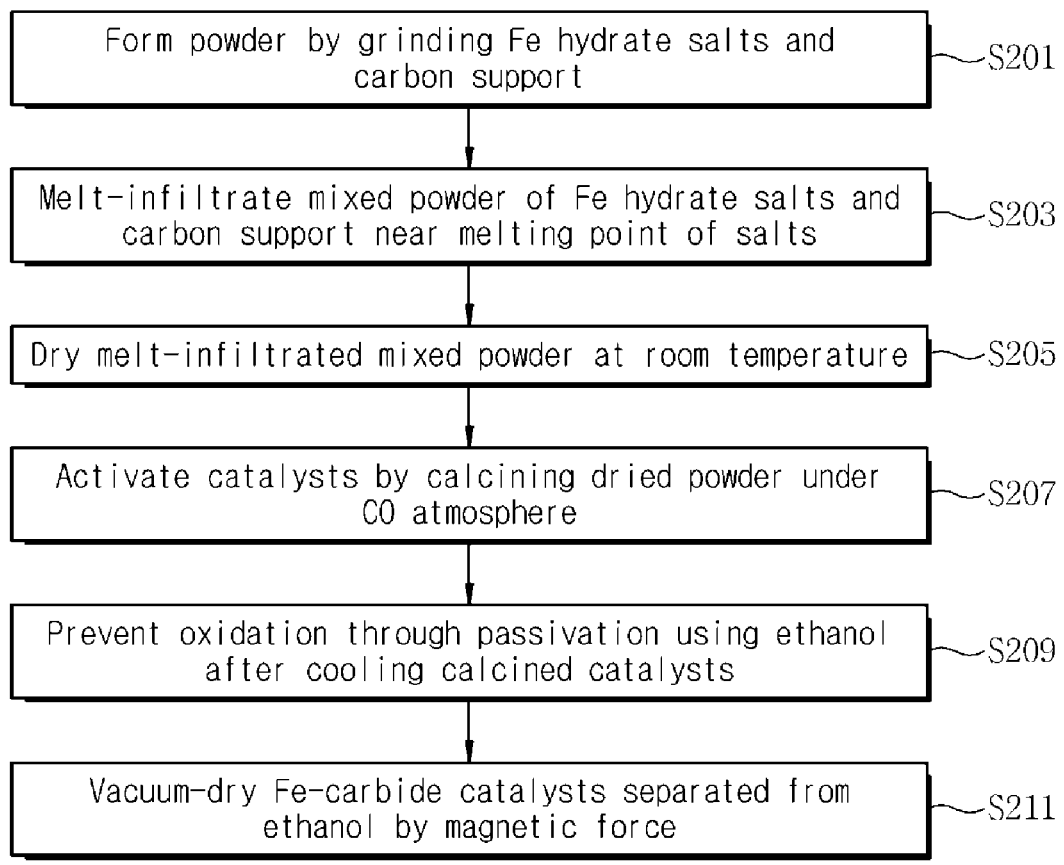
FIG. 2 is a flow diagram illustrating a method for preparing iron/carbon nanocomposite catalysts for Fischer-Tropsch reactions in accordance with an embodiment of the present invention.

FIG. 1 is a schematic view illustrating a preparation of iron/carbon nanocomposite catalysts for Fischer-Tropsch reactions in accordance with an embodiment of the present invention, and FIG. 2 is a flow diagram illustrating a method for preparing iron/carbon nanocomposite catalysts for Fischer-Tropsch reactions in accordance with an embodiment of the present invention.

Referring to FIGS. 1 and 2, the catalyst preparation method includes step of grinding iron hydrate salt, together with a mesoporous carbon support, and then performing melt-infiltration at a low temperature (steps 101, 201 and 203), step of calcining, decomposing and activating obtained nanocomposite powder of iron hydrate salt and carbon at a high temperature under a carbon monoxide atmosphere (steps 102, 205 and 207), step of stabilizing obtained iron/carbon (Fe/C) nanocomposite catalysts through passivation using ethanol (steps 103 and 209), and step of collecting the catalysts by using a magnet, discarding ethanol, and drying the catalysts through vacuum drying (steps 104 and 211).

Figure 3:
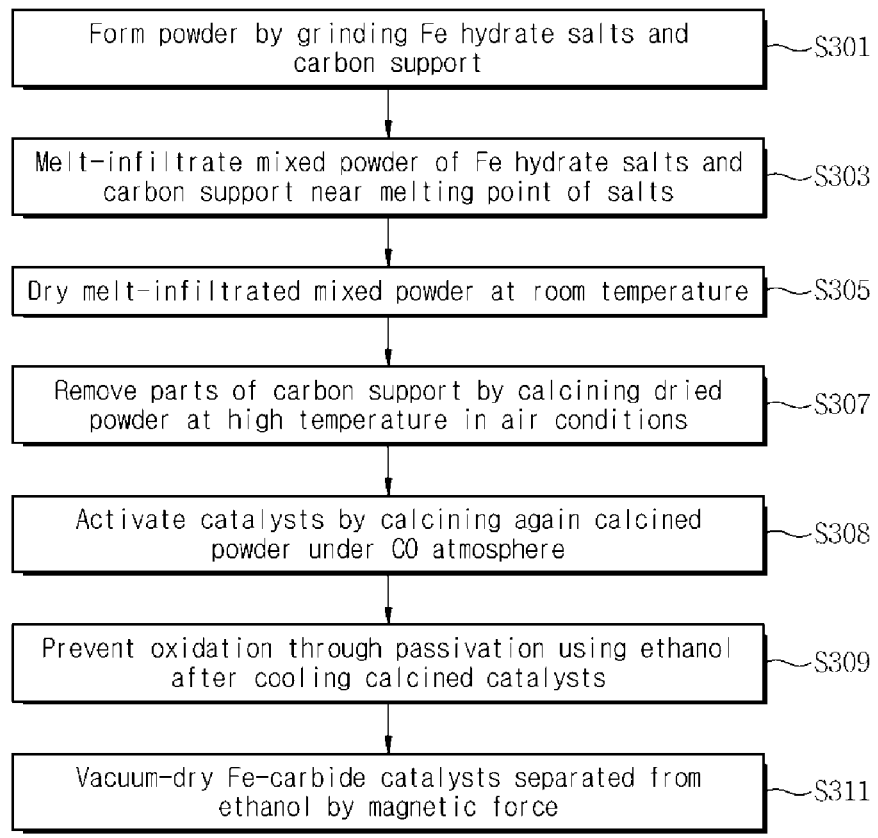
FIG. 3 is a flow diagram illustrating a method for preparing highly infiltrated iron/carbon (Fe/C) nanocomposite catalysts for Fischer-Tropsch reactions in accordance with an embodiment of the present invention.

Additionally, in another embodiment of the present invention, the above-discussed catalysts may be used for a selective production method of liquid hydrocarbons. In this method, the catalysts are supplied to high temperature FT synthesis reactions for selectively obtaining gasoline ($C_5$-$C_{12}$) among liquid hydrocarbons without any further hydrocraking process. Meanwhile, to enhance infiltration content of catalysts in comparison with carbon, the above-discussed catalyst preparation method may further include step of increasing iron content by removing parts of carbon through calcination in the air as shown in FIG. 3 to be described later.

Now, the preparation method of iron/carbon-based catalysts in an embodiment of this invention will be described in detail. This invention relates to iron/carbon (Fe/C) nanocomposite catalysts for high temperature Fischer-Tropsch (FT) synthesis reactions and to a preparation method thereof.

Iron (Fe) hydrate used at step 101 is a hydrated iron compound having a melting point of 30~100° C. Such iron hydrate may include, but not limited to, $Fe(NO_3)_3 9H_2O$ (d=1.6429 g/cm$^3$, m.p.=47.2° C.), $FeCl_3 6H_2O$ (d=1.82 g/cm$^3$, m.p.=37° C.), $FeSO_4 7H_2O$ (1.898 g/cm$^3$, m.p.=70° C.), and the like. Any compound having a lower melting point is hard to handle since it is in a liquid state at room temperature. Any compound having a 100° C. or more melting point may boil since it is infiltrated at a higher temperature than the boiling point of water. Particularly, such respective metal salts have intrinsic density values. So, by determining the amount of infiltration of a metal salt in consideration of the density of a metal salt and the pore volume of a mesoporous carbon support, it is possible to much uniformly infiltrate a salt. Also, a reactor can be selected according to the amount of a metal hydrate salt and a reaction temperature. Normally a reactor formed of stainless steel or polymer plastic such as polypropylene or Teflon may be used.

To melt and uniformly infiltrate iron hydrate salts into a support, it is important to adjust a temperature and maintain a pressure in a reactor. For a full infiltration of salts, an operating temperature may be adjusted to a temperature greater by 2~5° C. than a melting point of the salt. Further, reactions may proceed in the closed system such that a pressure caused by a steam pressure generated during such reactions may not become extinct. Meanwhile, a mesoporous carbon support may employ commercial activated carbon, commercial activated charcoal, commercial acetylene carbon black, synthetic mesoporous carbon (CMK), or the like. For uniform infiltration with suitable content (5~40%) for FT reactions, a pore volume of carbon support material may be preferably 0.2 cm$^3$/g or more. In addition, to further increase infiltration content of particles, carbon material having a higher pore volume is preferred.

Calcination conditions used at step 102 is important to make an iron carbide phase in which infiltrated iron hydrate salts are fully decomposed and hence have activity. A calcination temperature may be between 300~400° C., preferably 350° C., where particles have suitable sizes and activity. Activation gas may employ carbon monoxide, hydrogen, or mixed gas thereof, preferably pure carbon monoxide in view of catalyst activation. A calcination time is 1~24 hours for sufficient activation.

At step 103, passivation for stabilization of activated catalysts is important for subsequent application of deoxidized catalysts and has a function to block a reaction between catalysts and oxygen by using an organic solvent. Various solvents such as ethanol and mineral oil may be employed as an organic solvent, but water capable of oxidizing catalysts cannot be used. Passivation is performed through step of immersing catalysts into an organic solvent not to be exposed to oxygen under nitrogen or any other inert gas atmosphere. For later analysis or application to a fixed-bed reactor, easy-dryable ethanol is preferably used as a solvent. Iron/carbon catalysts are magnetic. Therefore, such catalysts can be easily separated from a solvent by using a magnet. After separation, the catalysts are dried again through a vacuum drying process and then may be used immediately or stored in a vacuum or nitrogen pack. The above-discussed iron hydrate salt may be added at the ratio of 0.5~4.5 with regard to the weight of a carbon support.

FIG. 3 is a flow diagram illustrating a method for preparing highly infiltrated iron/carbon (Fe/C) nanocomposite catalysts for Fischer-Tropsch reactions in accordance with an embodiment of the present invention.

Referring to FIG. 3, the preparation method of high-infiltrated catalysts includes step of forming powder by uniformly grinding iron hydrate salts and a carbon support (step 301), step of melt-infiltrating the mixed powder of the iron hydrate salts and the carbon support near a melting point of the salts in a reactor (step 303), step of drying the melt-infiltrated mixed powder at room temperature (step 305), step of removing parts of the carbon support by calcining the dried powder at a high temperature in air or oxygen conditions (step 307), step of activating catalysts by calcining again the calcined powder under a carbon monoxide atmosphere (step 308), step of preventing oxidation through passivation using ethanol after cooling the calcined catalysts to a room temperature (step 309), and step of vacuum-drying iron-carbide catalysts after separating the catalysts from ethanol by a magnetic force (step 311).

Particularly, step 307 is to increase infiltration content of particles. At this step, a heat treatment temperature may be more than 200° C. where metal salts start to be decomposed. Since calcination at a high temperature of 700° C. or more may cause serious inter-particle clustering which will be unfavorable to the use of catalysts, a temperature between 350~500° C. is suitable. Preferably, calcination is performed in the air in consideration of cost and stability. However, pure oxygen or mixed oxygen may be alternatively used in view of high reliability. A calcination time affects the amount of carbon removed. Therefore, a calcination time may be determined depending on final infiltration content of iron particles. Normally heat treatment is performed for 1~24 hours in order to obtain high-infiltrated catalysts of 50% or more.

Meanwhile, the iron/carbon infiltrated catalysts prepared through the above-discussed method can be supplied to a fixed-bed reactor to produce liquid hydrocarbons. By further injecting synthetic gas into the fixed-bed reactor without additional reduction/activation step, liquid hydrocarbons are produced. Now, a method for producing liquid hydrocarbons using FT synthesis reactions will be described in detail.

Usable synthetic gas is carbon monoxide, hydrogen, inert gas, methane, carbon dioxide, or the like. Mixed gas of carbon monoxide and hydrogen in the proportion 1:1 is preferred in view of yield of product. Also, synthetic gas is injected into the fixed-bed reactor at a gas hourly space velocity (GHSV) ranging between 3.0~15.0 $NL/g_{cat}/hr$. Any GHSV smaller than the above range may cause low productivity of liquid hydrocarbons per hour, and any GHSV greater than the above range may cause a decrease in a conversion rate of carbon monoxide. An operating temperature may range between 250~350° C. To enhance the conversion rate of carbon monoxide and to increase the yield of liquid hydrocarbons, a temperature between 310~350° C. is preferred.

In the FT synthesis reactions using ex-situ activated iron/carbon infiltrated catalysts, high temperature conditions of 300~600° C. have merits of a higher carbon monoxide conversion rate and of selective obtainability of gasoline ($C_5$-$C_{12}$) among liquid hydrocarbons. Therefore, the above-discussed catalysts can be favorably may be favorably applied to commercial processes of the high-temperature FT reactions.

First Embodiment: Preparation of Fe/Charcoal Catalysts [S/C=1.8]

For uniform and high dispersion of hydrated Fe salts into a carbon support, S/C ratio which is defined as the ratio of the amount of salts to that of carbon was selected as 1.8. Specifically, $Fe(NO_3)_3 9H_2O$ (Aldrich, 98+%, fw=404 g/mol, m.p.=47.2° C.) 57.9 g and activated charcoal (Aldrich, −100 mesh particle size, fw=12.01 g/mol) 32.0 g were placed in a mortar and sufficiently ground using pestle until they become uniform. Then, mixed black powder was put in a polypropylene vessel. The vessel was closed with a stopper and stored in a drying oven with a temperature of 50° C. for 24 hours. After ripening for 24 hours, mixed powder was dried at a room temperature and then ground again uniformly. By performing heat treatment using a calcination oven at 350° C. for 4 hours under a carbon monoxide atmosphere (a normal pressure, a fluid speed of 200 mL/min), iron-carbide (FeCx)/charcoal catalysts was obtained. Since such catalyst powder tends to be easily oxidized when exposed to the air, passivation was performed through steps of creating an airless atmosphere using nitrogen or inert gas such as helium and then immersing the catalyst powder into ethanol. Thereafter, the catalysts were separated from ethanol, dried in a vacuum oven, and finally stored in a vacuum pack. Iron content in the catalysts was measured through ICP-AES (inductively coupled plasma atomic emission spectroscopy) analysis. As a result, it was observed that 17.3 wt % iron is infiltrated.

Figure 4:
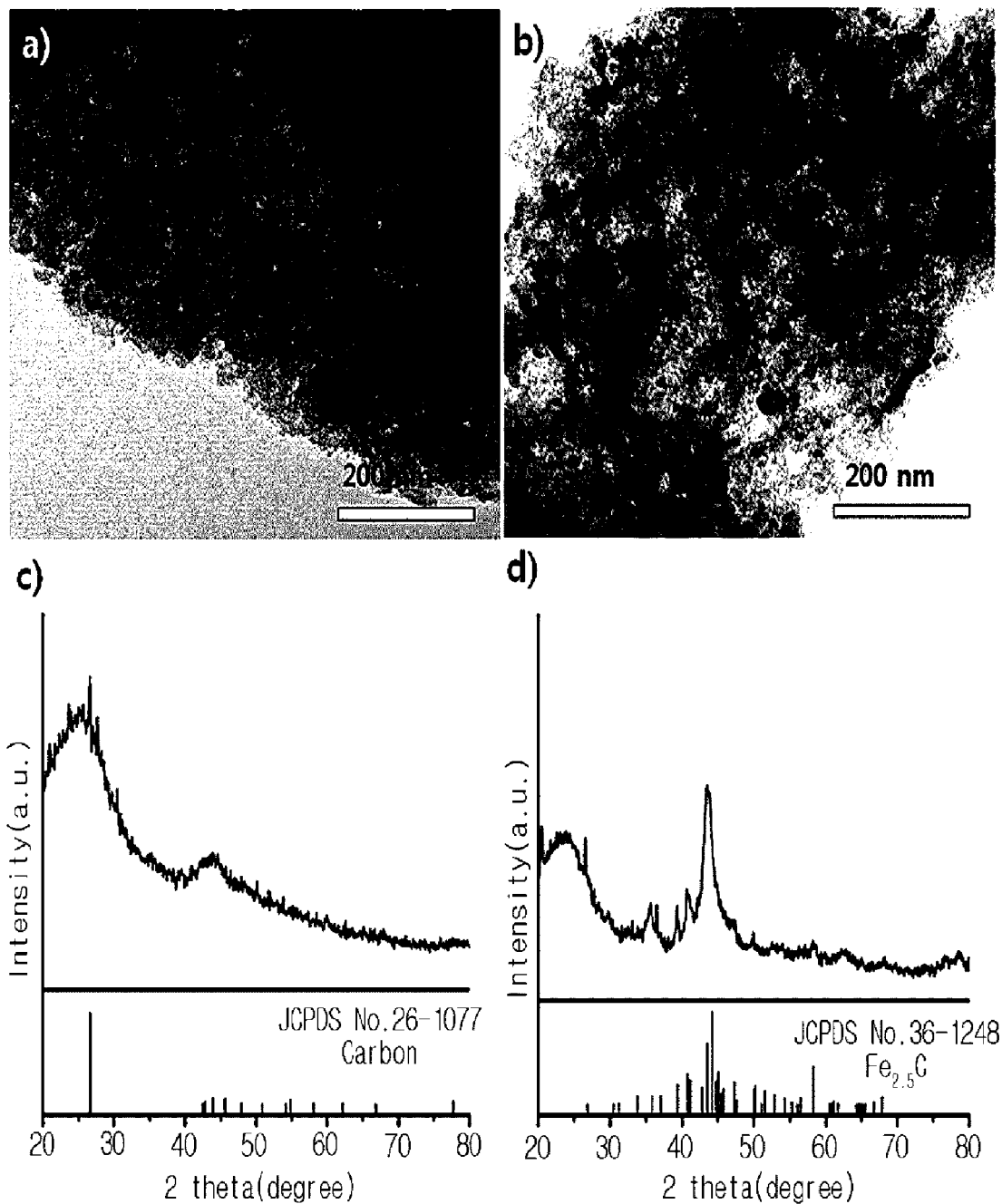
FIG. 4 shows TEM images and XRD spectrums of charcoal into which Fe hydrate salt is infiltrated in various conditions.

FIG. 4 shows TEM images and XRD spectrums of charcoal into which Fe hydrate salt is infiltrated in various conditions. Specifically, FIG. 4a shows a TEM image after Fe hydrate salt was infiltrated into a carbon support, and FIG. 4c shows XRD (X-ray diffraction) analysis results thereof. As shown in FIG. 4a, it was observed that Fe hydrate salts are sufficiently infiltrated with almost no exposure to carbon support surfaces. Also, as shown in FIG. 4c, it was observed that the infiltrated salt is amorphous. FIG. 4b shows a TEM image after the carbon support with infiltrated Fe hydrate salt was activated at a high temperature of 350° C. for under a carbon monoxide atmosphere, and FIG. 4d shows XRD analysis results thereof. Small active particles of about 10 nm were formed as shown in FIG. 4b, and most of them had activated Fe-carbide phase as shown in FIG. 4d.

FIRST COMPARATIVE EXAMPLE

Preparation of Fe/Charcoal Catalysts According to Variations in Infiltration Content of Salt One of ways to easily adjust infiltration content of Fe in finally obtained Fe/charcoal catalysts is to adjust the amount of Fe hydrate salt ($Fe(NO_3)_3 9H_2O$) with regard to the amount of initially supplied activated charcoal. To check resultant effects, several comparative experiments were conducted through variations in conditions. Specifically, using the same process as in the first embodiment and increasing S/C ratio to 0.8, 4.8, 10.9 and 28.9, resultant variations were observed.

Figure 5:
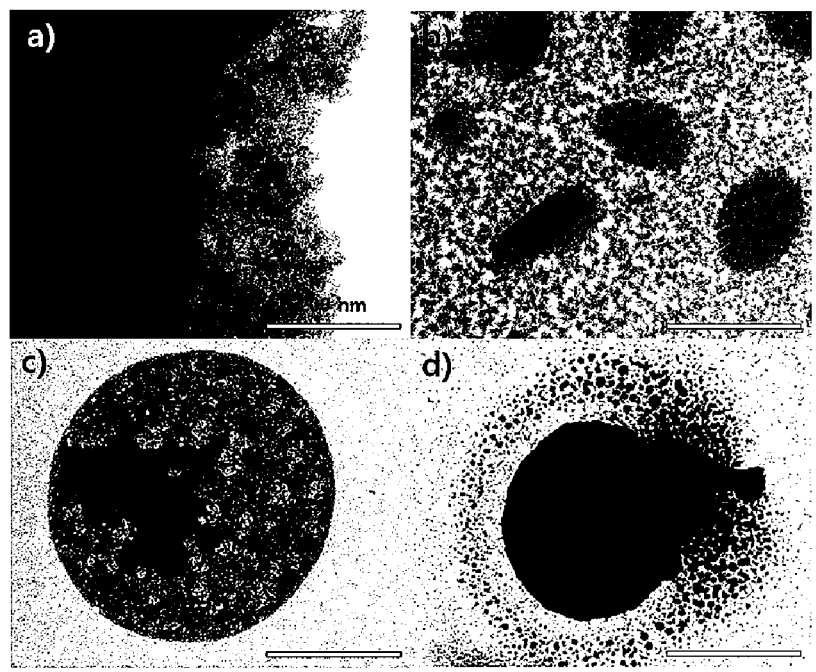
FIG. 5 shows TEM images of charcoal into which Fe hydrate salt is infiltrated according to various S/C ratios.

A pore volume of activated charcoal measured 0.85 $cm^3/g$ through the nitrogen adsorption-desorption experiment. In case of S/C ratio of 0.8, it was observed that a carbon support has enough pores for allowing good infiltration of all Fe hydrate salts as seen from a TEM image in FIG. 5a. However, in case of S/C ratio of 4.8 or more, it was observed that a lot of salts remain on surfaces of a support and moreover the structure of a carbon support collapses due to incidentally produced high concentration nitric acid as seen from TEM images in FIGS. 5b, 5c and 5d.

Figure 6:
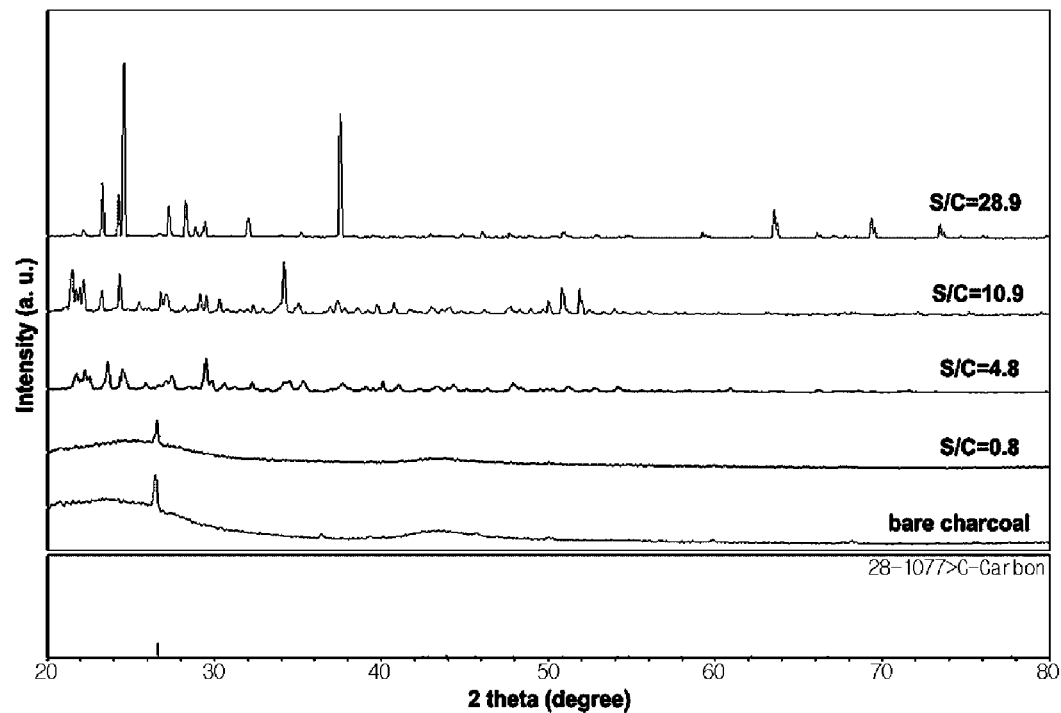
FIG. 6 shows XRD spectrums of catalysts infiltrated according to various S/C ratios.

Similarly, as seen from XRD analysis results in FIG. 6, crystalline peaks strongly emerged according as content of salts to be infiltrated was increased. This tells that Fe hydrate salts are not infiltrated into pores of a carbon support, but a lot of crystalline salts still remain on particle surfaces of the support.

SECOND COMPARATIVE EXAMPLE

Figure 7:
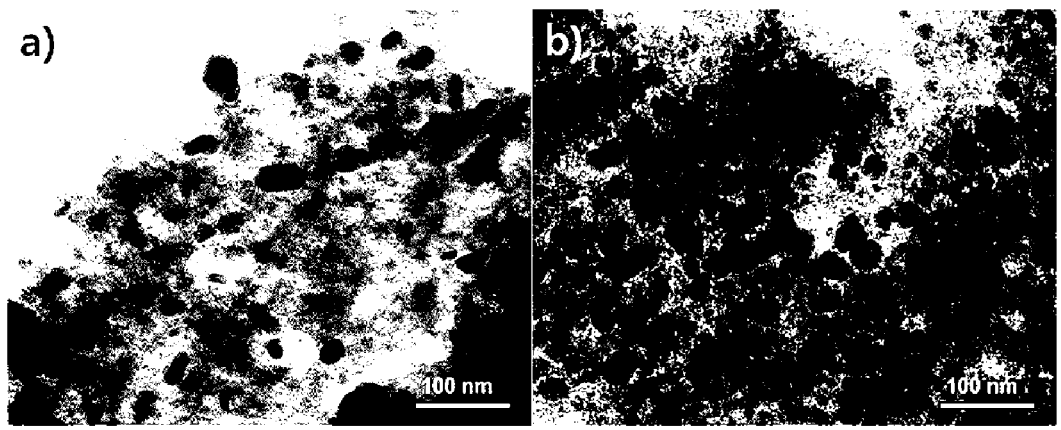
FIG. 7 shows TEM images of Fe/charcoal [S/C ratio=1.8] infiltrated catalysts according to calcination conditions under a nitrogen or hydrogen atmosphere.
Figure 8:
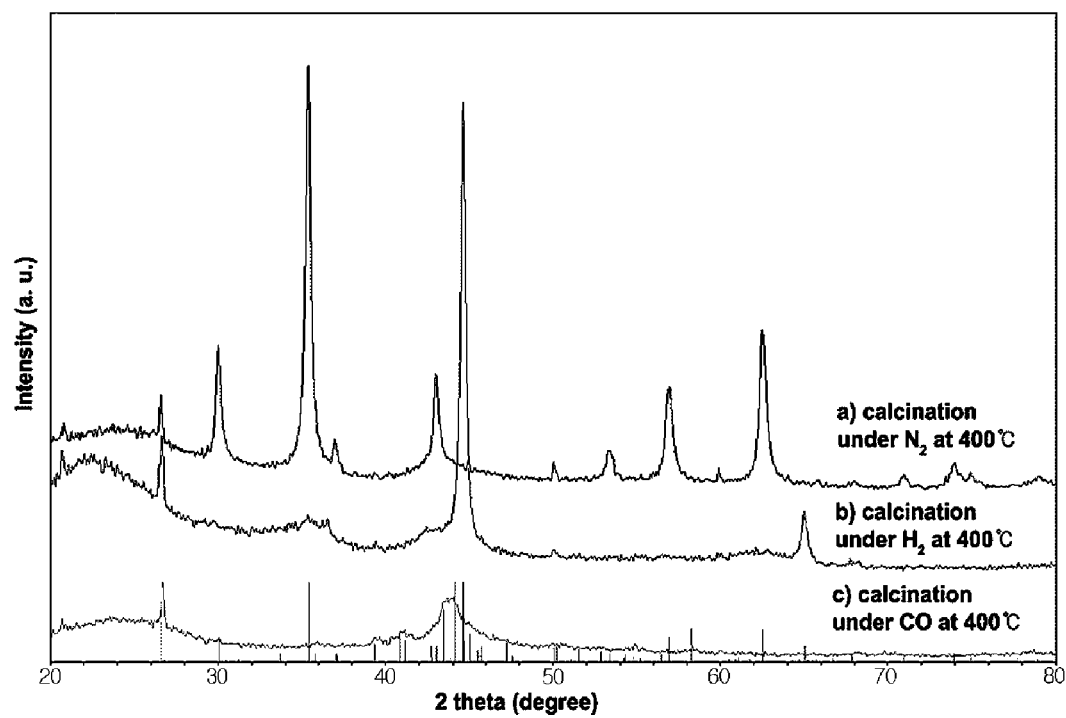
FIG. 8 shows XRD spectrums of Fe/charcoal [S/C ratio=1.8] infiltrated catalysts according to calcination conditions under a nitrogen, hydrogen or carbon monoxide atmosphere.

Variations of Fe/Charcoal Catalysts [S/C ratio=1.8] According to Ex-situ Activation Calcination Conditions Size and phase of catalyst particles in Fe/charcoal infiltrated catalysts may be greatly affected by ex-situ calcination atmosphere and temperature conditions. For comparison with the first embodiment, calcination was carried out for Fe hydrate salt infiltrated catalysts [S/C ratio=1.8] under nitrogen and hydrogen atmospheres, not under a pure carbon monoxide atmosphere. As the result of calcination at 400° C. for 4 hours under a nitrogen atmosphere, it was observed that particles are not uniform in shape and range between 10~30 nm in size as seen from a TEM image in FIG. 7a. On the contrary, in case of a hydrogen atmosphere, it was observed that particles are uniform as nearly rounded shapes and have similar size of about 20 nm as shown in FIG. 7b. Also, as seen from XRD analysis results in FIG. 8, it was observed that $Fe_3O_4$ (magnetite) particles are formed in case of calcination under a nitrogen atmosphere, and pure Fe (iron) is formed in case of calcination under a hydrogen atmosphere.

THIRD COMPARATIVE EXAMPLE

Variations According to Use of Various Carbon Supports

Figure 9:
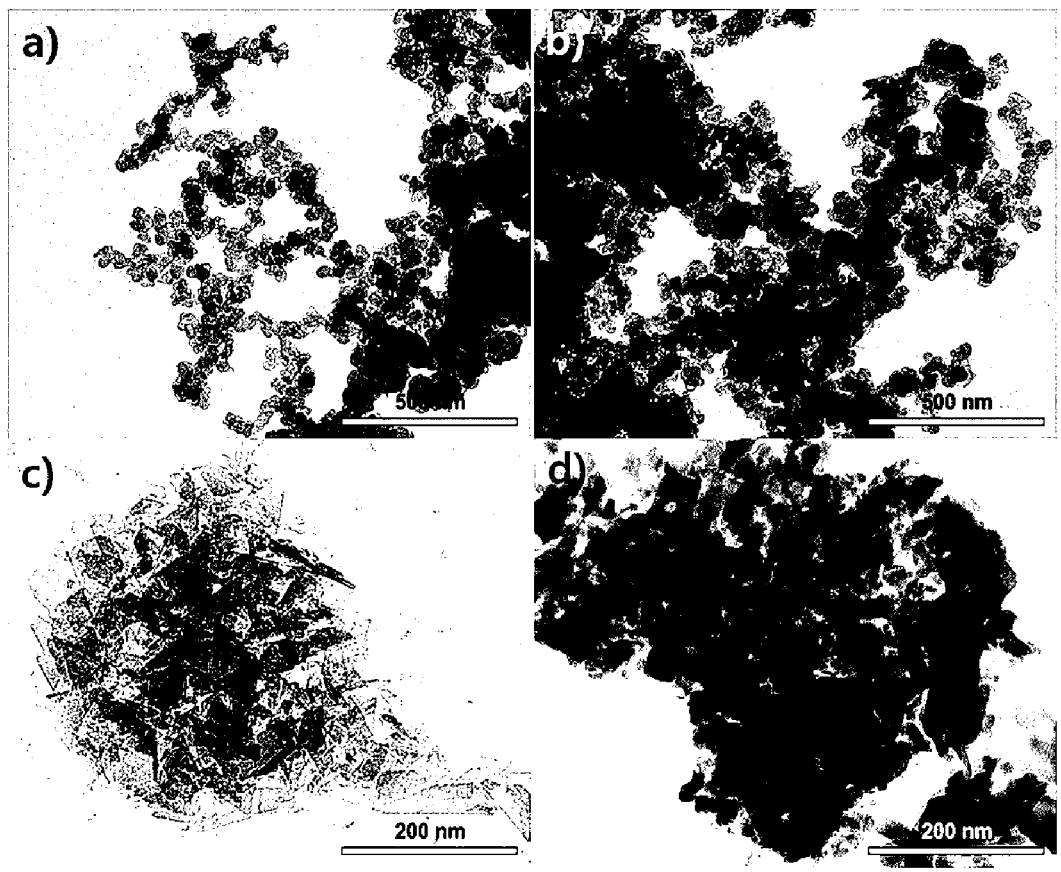
FIG. 9 shows TEM images of Fe salt infiltrated acetylene carbon black, Fe salt infiltrated activated carbon, and catalyst phases thereof after calcination under a 400° C. nitrogen atmosphere.

Various types of carbon may be used as a support, and the above method in the first embodiment may be equally applied to such carbon supports. For comparison, S/C ratio was selected as 1.8, and acetylene carbon black (STREM Co. Ltd., pore volume=0.24 cm$^3$/g, BET SSA=73 m$^2$/g) and activated carbon (STREM Co. Ltd., pore volume=0.79 cm$^3$/g, BET SSA=1381 m$^2$/g) were used respectively instead of activated charcoal. After infiltration in case of using acetylene carbon as a support, it was observed that salts become lumpy on carbon surfaces as seen from a TEM image in FIG. 9a because of a small pore volume of the carbon support. Even after calcination under a nitrogen atmosphere, lumpy particles were still observed as shown in FIG. 9b. On the contrary, in case of using activated carbon as a support, metal salts were rarely observed on carbon surfaces as seen from a TEM image in FIG. 9c because of a great pore volume of the support. However, it was observed that non-uniform particles are considerably formed as calcination is performed under a nitrogen atmosphere.

FOURTH COMPARATIVE EXAMPLE

Variations According to Use of Fe Chloride Hydrate Salt

Figure 10:
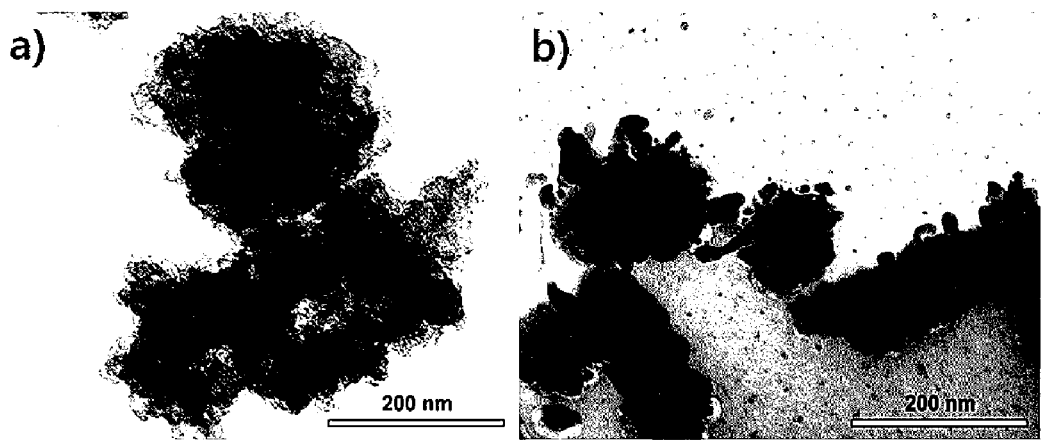
FIG. 10 shows TEM images of Fe chloride hydrate salt infiltrated activated charcoal [S/C ratio=1.2] and a catalyst phase thereof after calcination under a 400° C. nitrogen atmosphere.
Figure 11:
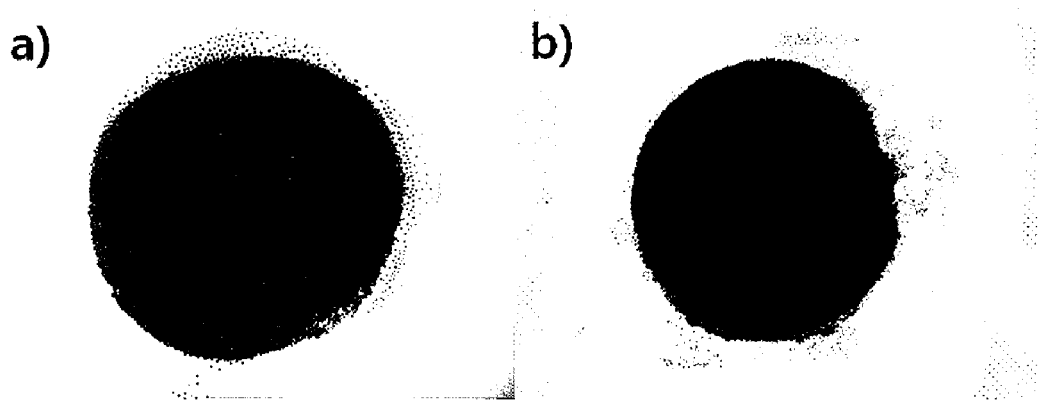
FIG. 11 shows TEM images of commercial activated carbon sphere (diameter 0.35 mm) and a catalyst phase thereof after melt-infiltration.

A comparative experiment for infiltrating $FeCl_3 6H_2O$ (Aldrich, 98+%, fw=270.3 g/mol, m.p.=37° C.) salts, instead of $Fe(NO_3)_3 9H_2O$, into a charcoal support was conducted using the same method as the first embodiment. S/C ratio was selected as 1.2 and an infiltration temperature was lowered to 40° C. since the intrinsic density of $FeCl_3 6H_2O$ is 1.82 cm$^3$/g which is somewhat greater than 1.6429 cm$^3$/g of $Fe(NO_3)_3 9H_2O$. As the result of experiment, it was observed that salts are infiltrated well into a carbon support as seen from a TEM image in FIG. 10a. However, shape and size of particles were more non-uniform than $Fe(NO_3)_3 9H_2O$ salts were used in calcination under a nitrogen atmosphere.

Second Embodiment: Preparation of Granule Type Fe/Carbon Catalysts

When powder type catalysts are used in a scaled-up fixed-bed reactor, reaction may progress unfavorably due to increased pressure-drop. The use of granule having a relatively greater size ranging from hundreds to thousands of micrometers can decrease pressure-drop when reactant flows at a high flow rate. Various types of carbon such as pellet or granule as well as powder can be applied to a support in this invention. The amount of Fe hydrate salts and the amount of a carbon support are the same as in the first embodiment. However, instead of grinding metal salts and a carbon support together using pestle, metal salts may be ground first using pestle. Then the ground salts are mixed with carbon sphere (Pure Sphere Co., diameter 0.35 mm) in a polypropylene vessel and infiltrated. Post processing is the same as in the first embodiment.

Third Embodiment: Preparation of High-infiltrated Catalysts

Figure 12:
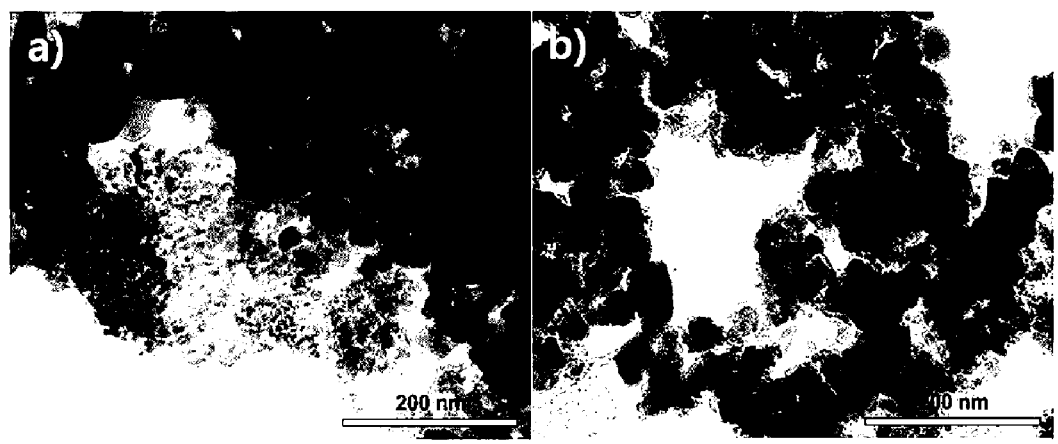
FIG. 12 shows TEM images of Fe/charcoal [S/C ratio=1.8] infiltrated catalysts in case of calcination in the air and in case of reactivation under a carbon monoxide atmosphere after calcination in the air.

To obtain catalysts into which iron is highly infiltrated, parts of carbon used as a support may be removed through heat treatment in the air before activation using carbon monoxide after iron hydrate salts are infiltrated in the same process as in the first embodiment. Specifically, by heat-treating dry mixed powder in a calcination oven at 400° C. for 4 hours under an air atmosphere after infiltration for 24 hours, carbon was partially removed and hence $Fe_2O_3$/C catalysts with high-infiltrated Fe were obtained. Thereafter, through activation at 350° C. for 4 hours under a carbon monoxide atmosphere, catalysts with high-infiltrated Fe-carbide particles were obtained. A TEM image in FIG. 12a shows that the size of particles tends to be increased according as carbon is removed. As shown in FIG. 12b, it was observed that activated Fe-carbide particles have a size of about 50 nm and only a part of carbon adheres on the periphery. Also, in ICP-AES for analyzing the content of infiltrated Fe particles, it was observed that Fe content is considerably increased to 58.0 wt %.

Fourth Embodiment: Liquefaction Reaction Using Fe/Charcoal Catalysts $FeC_x$/charcoal catalysts obtained finally by activating catalysts prepared from Fe/charcoal [S/C ratio=1.8] in the first embodiment were applied to the high-temperature FT synthesis reactions. A fixed-bed reactor was used, and reaction processes were carried out using a PC-controllable automated system. Catalysts 0.8 g was loaded, just after dried, into the reactor having an inner diameter of 5 mm. To prevent hot spot from being generated due to a serious exothermic reaction of catalysts, glass bead 1.6 g was supplied together. While synthetic gas in which the ratio of hydrogen to carbon monoxide is maintained to 1:1 was injected at 80 cc/min into the reactor having an operating pressure of 15 atmospheres and GHSV of 6.0 $NL/g_{cat}$/hr, the high-temperature FT synthesis reactions were performed at 340° C. without any additional reduction process in the reactor. Reaction results for 48 hours are shown in Table 1 and FIG. 13.

TABLE 1

| CO Conv. (Total) | CO to $CO_2$ | CO to HC | $H_2$ Conv. (Overall) | $CO_2$ Sel. (C mol %) | $CH_4$ Sel. (C mol %) | $C_2$-$C_4$ Sel. (C mol %) | $C_5$ Sel. (C mol %) |
|---|---|---|---|---|---|---|---|
| 91.6 | 38.0 | 53.6 | 75.6 | 41.4 | 10.5 | 19.2 | 28.9 |

Figure 13:
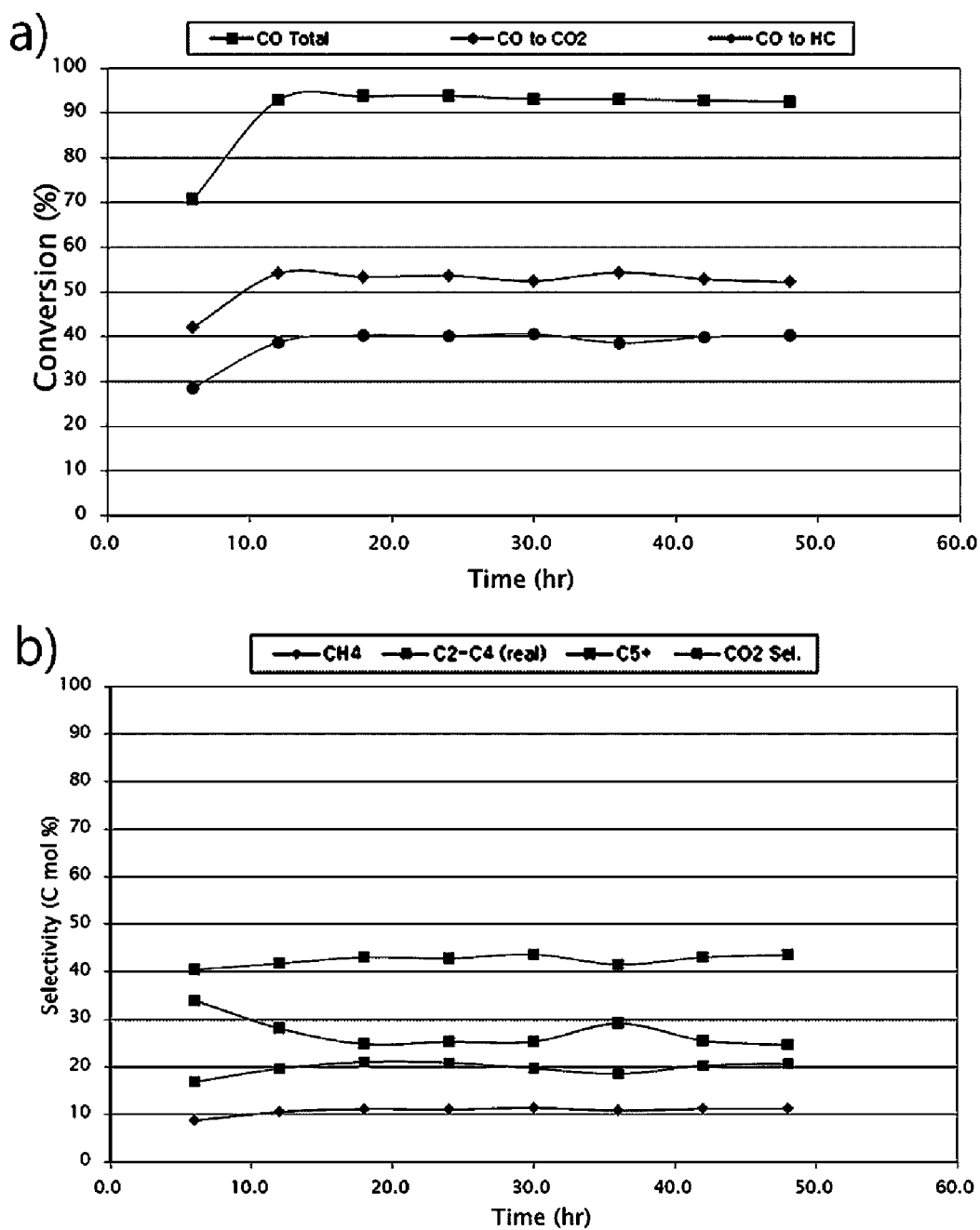
FIG. 13 shows graphs of hourly carbon monoxide conversion rate and hourly product selectivity.
Figure 14:
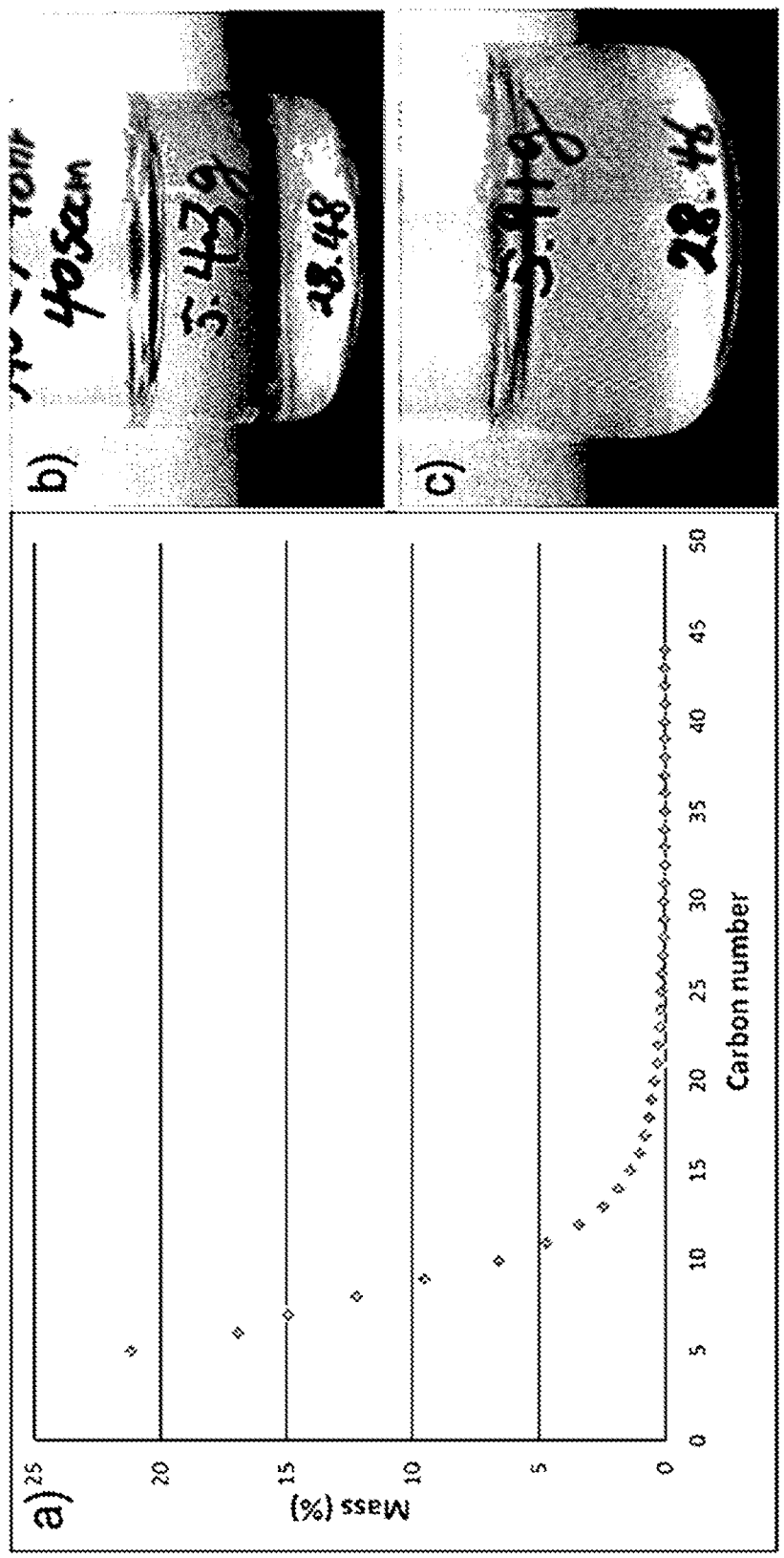
FIG. 14 shows an SIMDIS analysis graph of liquid products and photos of produced oil and water.

As shown in Table 1 and FIG. 13, when the FT synthesis reactions of this invention were performed, it was observed that a carbon monoxide conversion rate reaches 90% and excellent product selectivity is achieved by obtaining only liquid hydrocarbons and water as shown in FIGS. 14b and 14c without formation of solid-phase wax. Additionally, as seen from FIG. 14a, SIMDIS (simulated distillation) analysis results of liquid products show very high selectivity of $C_5$~$C_{12}$ and high selectivity of 90% compared to total liquid oil products.

FIFTH COMPARATIVE EXAMPLE

Liquefaction Reaction Using Fe/Charcoal Catalysts

Figure 15:
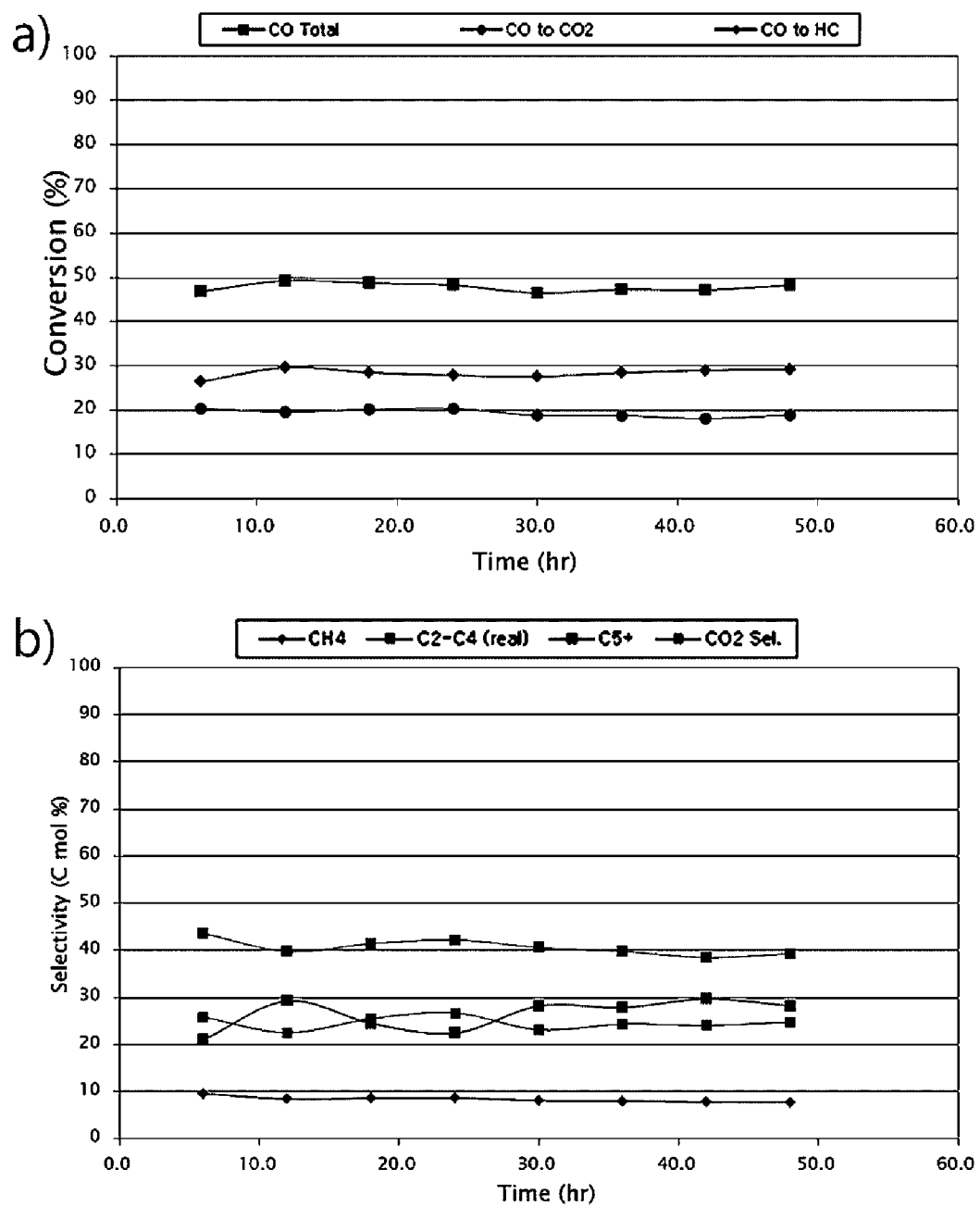
FIG. 15 shows graphs of hourly carbon monoxide conversion rate and hourly product selectivity in reaction conditions of 300° C. and GHSV=3.0 $NL/g_{cat}/hr$.
Figure 16:
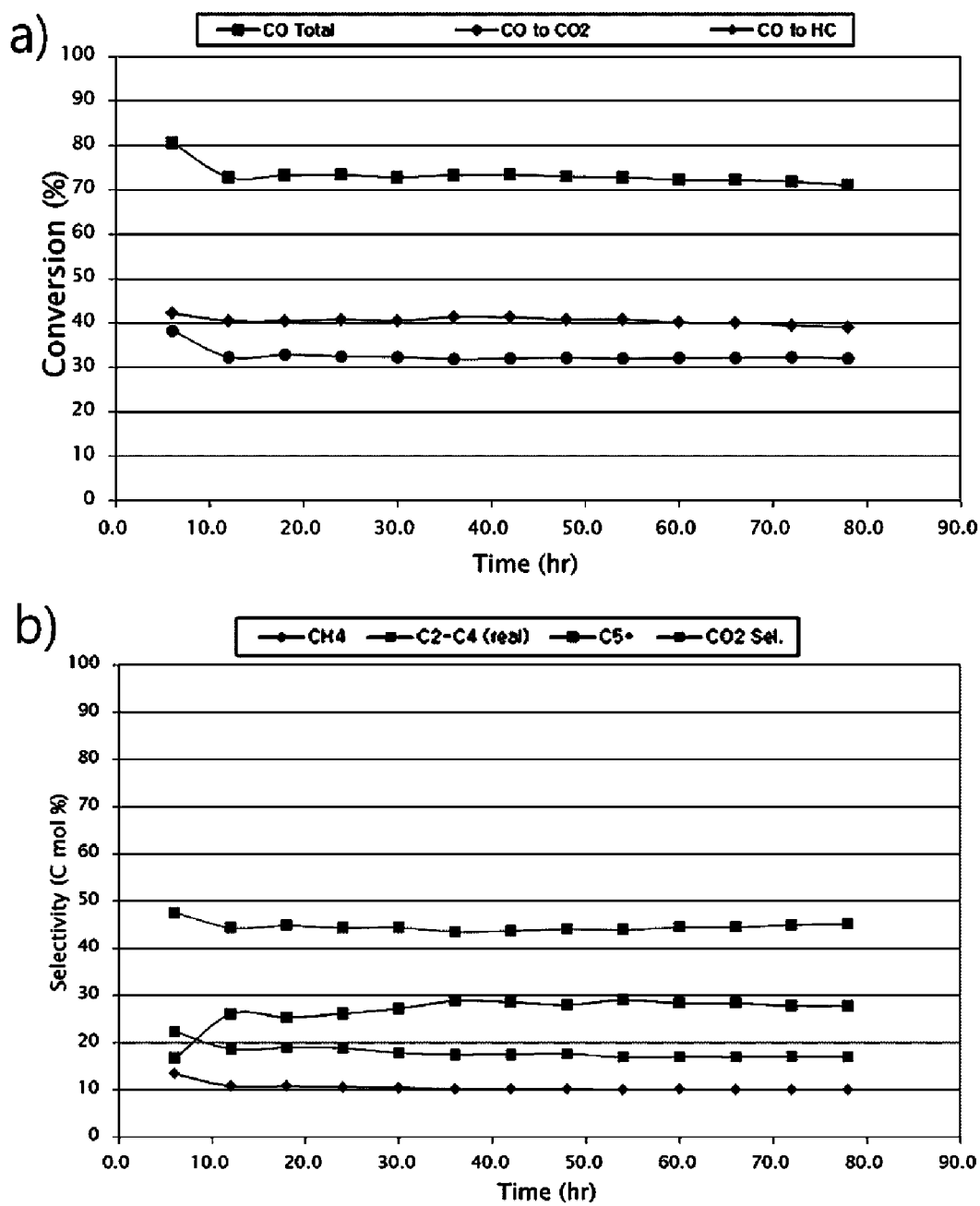
FIG. 16 shows graphs of hourly carbon monoxide conversion rate and hourly product selectivity in reaction conditions of 330° C. and GHSV=4.5 $NL/g_{cat}/hr$.

Like the fourth embodiment, catalysts prepared through the method in the first embodiment were applied to the high-temperature FT synthesis reactions in various temperature conditions. When an operating temperature in the FT synthesis reactions was lowered to 300° C. as shown in FIG. 15, a carbon monoxide conversion rate was sharply decreased to about 50% despite a reduction of GHSV to 3.0 NL/$g_{cat}$/hr. On the contrary, in case of 330° C. reactions as shown in FIG. 16, a carbon monoxide conversion rate was at a high level of about 70% despite an increase of GHSV to 4.5 NL/$g_{cat}$/hr.

As fully discussed hereinbefore, the present invention allows obtaining high-active Fe/carbon nanocomposite catalysts, for high temperature FT reactions, in which activated Fe-carbide particles are infiltrated with 1~40 wt % into a mesoporous carbon support. Such catalysts can be prepared through a melt-infiltration method and an ex-situ activation process under a carbon monoxide atmosphere and thus can be obtained easily, quickly and in large amounts in comparison with a conventional co-precipitation method. Further, no use of additional solvent can improve work stability and reduce a burden of environmental pollution due to solvent treatment. Also, thermally stable, optimum, high-active, Fe/carbon-supported catalysts can be obtained through easy controls of particle size, supported content, particle crystallizability, etc. And also, liquid hydrocarbons which are structurally stable to heat during high temperature FT reactions of 300° C. or more can be obtained selectively in a gasoline range and high yield on the basis of the above catalysts. Besides, no formation of solid-phase wax allows liquid hydrocarbons to be applied immediately without a hydrocracking process.

While this invention has been particularly shown and described with reference to an exemplary embodiment thereof, it will be understood by those skilled in the art that various changes in form and details may be made therein without departing from the spirit and scope of the invention as defined by the appended claims.

What is claimed is:

1. A method for preparing iron/carbon nanocomposite catalysts for Fischer-Tropsch synthesis reactions, the method comprising steps of:
   mixing iron hydrate salts and a mesoporous carbon support to form a mixture;
   infiltrating the iron hydrate salts into the carbon support through melt infiltration of the mixture near a melting point of the iron hydrate salts;
   forming iron-carbide particles infiltrated into the carbon support through calcination of the iron hydrate salts infiltrated into the carbon support under a first atmosphere; and
   vacuum-drying the iron-carbide particles after passivation using ethanol.

2. The method of claim 1, further comprising steps of:
   between the infiltrating step and the particle forming step, drying the melt-infiltrated mixture; and
   removing parts of the carbon support and forming iron oxide by calcining the dried mixture in a second atmosphere.

3. The method of claim 1, wherein the melting point of the iron hydrate salts ranges between 30~100° C.

4. The method of claim 1, wherein the iron hydrate salt is one of $Fe(NO_3)_3 9H_2O$, $FeCl_3 6H_2O$ and $FeSO_4 7H_2O$.

5. The method of claim 1, wherein the support is mesoporous carbon having a pore volume of 0.2 $cm^3$/g or more.

6. The method of claim 1, wherein the iron hydrate salts are added at the ratio of 0.5~4.5 with regard to the weight of the carbon support.

7. The method of claim 1, wherein an ex-situ activation temperature of the catalysts ranges between 300~600° C.

8. The method of claim 1, wherein an ex-situ activation time of the catalysts ranges between 1~24 hours.

9. The method of claim 2, wherein the second atmosphere is one of an air atmosphere, an oxygen atmosphere, and a mixed oxygen atmosphere of inert gas and oxygen.

10. The method of claim 1, wherein the mixing step includes grinding the iron hydrate salts and the carbon support.

11. The method of claim 1, wherein the infiltrating step is performed at an operating temperature greater by 2~5° C. than the melting point of the salt in a closed system.

12. Iron/carbon nanocomposite catalysts prepared by the method of claim 1.

13. A method for producing liquid hydrocarbons using Fischer-Tropsch synthesis reactions, the method comprising steps of:
   loading the iron/carbon nanocomposite catalysts prepared by the method of claim 1 into a fixed-bed reactor; and
   injecting synthetic gas into the fixed-bed reactor at a high temperature without additional reduction or activation process.

14. The method of claim 13, wherein the synthetic gas is injected into the fixed-bed reactor at a gas hourly space velocity (GHSV) ranging between 3.0~15.0 NL/$g_{cat}$/hr.

* * * * *